United States Patent [19]

McCusker

[11] Patent Number: 5,399,823

[45] Date of Patent: Mar. 21, 1995

[54] MEMBRANE DOME SWITCH WITH TACTILE FEEL REGULATOR SHIM

[75] Inventor: David R. McCusker, Shingle Springs, Calif.

[73] Assignee: MiniMed Inc., Sylmar, Calif.

[21] Appl. No.: 149,859

[22] Filed: Nov. 10, 1993

[51] Int. Cl.⁶ .......................................... H01H 13/14
[52] U.S. Cl. ................................ 200/521; 200/512; 200/516
[58] Field of Search ............... 200/521, 512, 515, 516, 200/517, 518, 520

[56] References Cited

U.S. PATENT DOCUMENTS

| | | | |
|---|---|---|---|
| 2,897,327 | 7/1959 | De Smidt | 200/520 |
| 4,056,701 | 11/1977 | Weber | 200/517 |
| 4,263,485 | 4/1981 | Corwin | 200/512 |
| 4,794,215 | 12/1988 | Sawada et al. | 200/512 |
| 4,892,988 | 1/1990 | Ishii | 200/516 |
| 5,224,591 | 7/1993 | Santo et al. | 200/512 |

*Primary Examiner*—Henry J. Recla
*Assistant Examiner*—David J. Walczak
*Attorney, Agent, or Firm*—Kelly Bauersfeld & Lowry

[57] ABSTRACT

A membrane dome switch is disclosed which includes a tactile feel regulator shim to provide an enhanced and consistent tactile feedback in response to fingertip switch depression. The membrane dome switch includes a conductive domed spring member mounted in a sandwich or laminant array between an underlying circuit layer having a conductive circuit pattern thereon and an overlying shield layer. Fingertip pressure applied to the shield layer is effective to deform the spring member to momentarily close a circuit path on the circuit layer. The tactile feel shim is interposed between the spring member and the overlying shield layer, and functions to provide improved tactile feedback sensation during switch operation. In the preferred form, a plurality of domed spring members are provided for selective fingertip depression to control and/or program an electronic device such as a medication infusion pump, and the regulator shim comprises a multi-legged web having individual legs defining a plurality of foot pads positioned for respectively overlying the domed spring members.

4 Claims, 3 Drawing Sheets

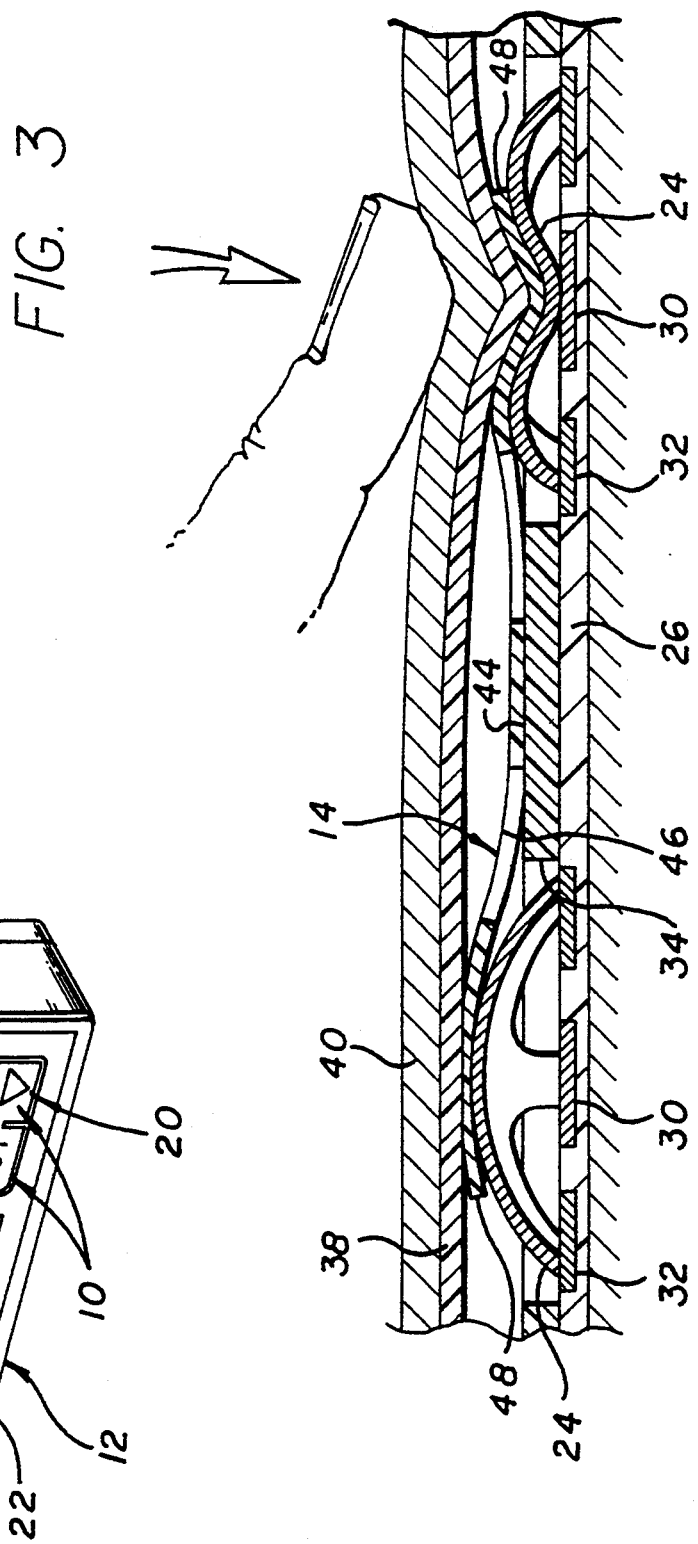
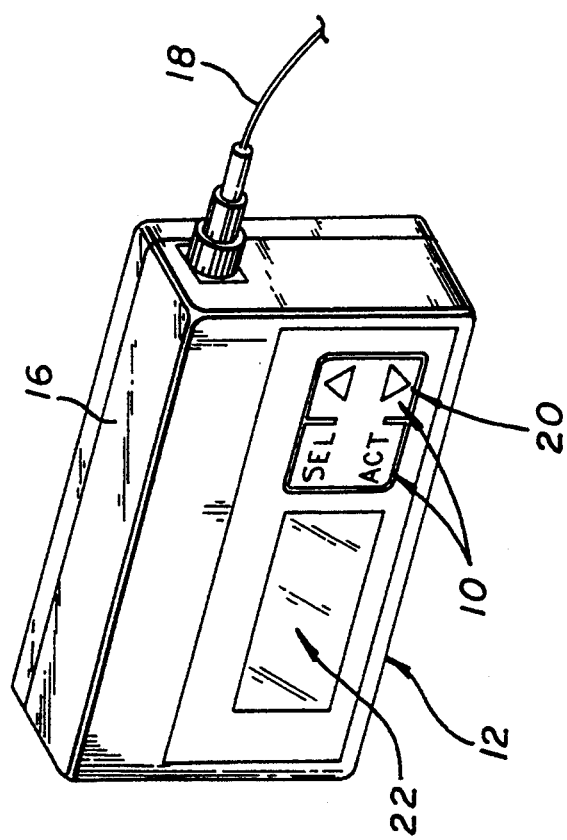

MEMBRANE DOME SWITCH WITH TACTILE FEEL REGULATOR SHIM

BACKGROUND OF THE INVENTION

1. Field of the Invention

The present invention relates generally to improvements in membrane dome switches of the type having one or more conductive spring members adapted for selective operation in response to fingertip pressure applied to a graphics overlay membrane, and more particularly to an improved membrane dome switch designed for enhanced and consistent tactile feedback sensation in response to fingertip switch depression.

Membrane dome switches are generally known in the art, particularly for use in operating a variety of electronic products, including hand-held and desktop devices such as calculators, computers, programmers, and the like. Such membrane dome switches typically comprise a conductive dome-shaped spring disk retained in a sandwich array between an underlying circuit layer having a conductive circuit pattern formed thereon, and an overlying shield layer. Fingertip pressure applied to predetermined points or regions of the shield layer is effective to deform the spring disk in a manner contacting the circuit layer, thereby achieving momentary closure of a circuit path for purposes of operating the electronic device.

In most designs, the overlying shield layer is covered in turn by a graphics overlay membrane or display panel which has appropriate operational instructions and/or indicia to facilitate fingertip depression of one or more dome switches. The graphics overlay membrane and the shield layer are sufficiently flexible in a direction perpendicular to the planes thereof to accommodate relatively easy switch operation.

Although membrane dome switches have enjoyed widespread use in modern electronic products, inconsistent tactile feedback sensation during switch operation can result in difficulties and/or frustrations in manipulating the dome switches to operate the electronic device. That is, the domed spring disks are normally maintained in correct alignment between the shield and circuit layers by positioning the spring disks within apertures formed in a retainer layer sandwiched between the circuit and shield layers. Variations in spring disk height as a result of normal manufacturing tolerances, relative to the thickness of the retainer layer, can have an adverse impact on tactile feedback fingertip sensation. Such tactile feedback is, of course, highly desirable since it provides a user with positive confirmation of switch depression.

More specifically, a spring disk which is too short relative to the thickness of the retainer layer can require a substantial downward force to be applied to the graphics membrane and shield layer in order to deform the spring disk sufficiently to close a circuit path. By contrast, when the spring disk is too tall relative to the retainer layer, the spring disk can be preloaded by the shield layer with the result that the spring disk operation can be inconsistent. In either case, dimensional variations on the order of a few thousandths of an inch can cause tactile feedback sensation to be significantly reduced or lost altogether.

There exists, therefore, a significant need for improvements in and to membrane dome switches of this general type. It is accordingly the primary objective of the present invention that it provide a membrane dome switch having a positive and easily detected tactile feedback sensation which is provided to the user notwithstanding normal dimensional variations present in domed spring disks. It is also an objective that the advantages and objectives of the membrane dome switch of the present invention be achieved without incurring any substantial relative disadvantage.

SUMMARY OF THE INVENTION

The disadvantages and limitations of the background art discussed above are overcome by the present invention. In accordance with this invention, an improved membrane dome switch includes a tactile feel regulator shim which has been found to provide the assembled dome switch with an enhanced and consistent tactile feedback sensation. As a result, the improved membrane dome switch of the present invention can be operated quickly and easily, while providing positive and easily detected feedback sensation confirming switch operation in a positive manner.

In the preferred form of the invention, a plurality of conductive spring members such as domed spring disks are mounted in stacked relation between an underlying circuit layer having a conductive circuit pattern formed thereon, and an overlying shield layer. The spring disks are positioned in predetermined alignment between the circuit and shield layers by means of an intermediate retainer layer having a plurality of cut-outs or apertures formed therein for individually receiving and retaining the spring disks.

A graphics overlay membrane or display panel having preprinted indicia formed thereon is normally mounted over the shield layer, with said indicia defining depression sites or regions for fingertip depression to deform a selected one of the underlying spring disks. Such fingertip depression applied to the selected spring disk, through the graphics membrane and shield layer, is effective to press the spring disk against the circuit layer in a manner achieving momentary closure of a circuit path.

The tactile feel regulator shim comprises a thin web of nonconductive sheet material interposed between the spring disks and the overlying cover layer or layers, such as the shield layer. In the preferred form, this web has a multi-legged geometry defining a plurality of legs which project outwardly from a central region and terminate in foot pad shims positioned generally over each respective one of spring disks. The central region of the multi-legged web is suitably anchored as by adhesive attachment to the retainer layer, whereas the foot pad shims remain unattached to and thus float between the spring disks and the shield layer.

During operation of the membrane switches, the foot pad shims have been found to result in a highly consistent and easily detectable feedback sensation each time a selected switch is depressed. Manipulation of the dome switches is thus confirmed to facilitate operation and control of the electronic device.

Other features and advantages of the present invention will become more apparent from the following detailed description. It may therefore be seen that the present invention teaches an improved membrane dome switch having a positive and easily detected tactile feedback sensation which is provided to the user notwithstanding normal dimensional variations present in domed spring disks. The advantages and objectives of the membrane domed switch of the present invention

DESCRIPTION OF THE DRAWINGS

These and other advantages of the present invention are best understood with reference to the drawings, in which:

FIG. 1 is a perspective view illustrating an electronic device such as a programmable medication infusion pump for use in administering a selected medication to a patient, wherein the electronic device includes a plurality of membrane dome switches for programmable operation thereof;

FIG. 3 is a sectional view illustrating assembled components of the membrane dome switches of FIG. 2.

DETAILED DESCRIPTION OF THE PREFERRED EMBODIMENT

Figure 2:
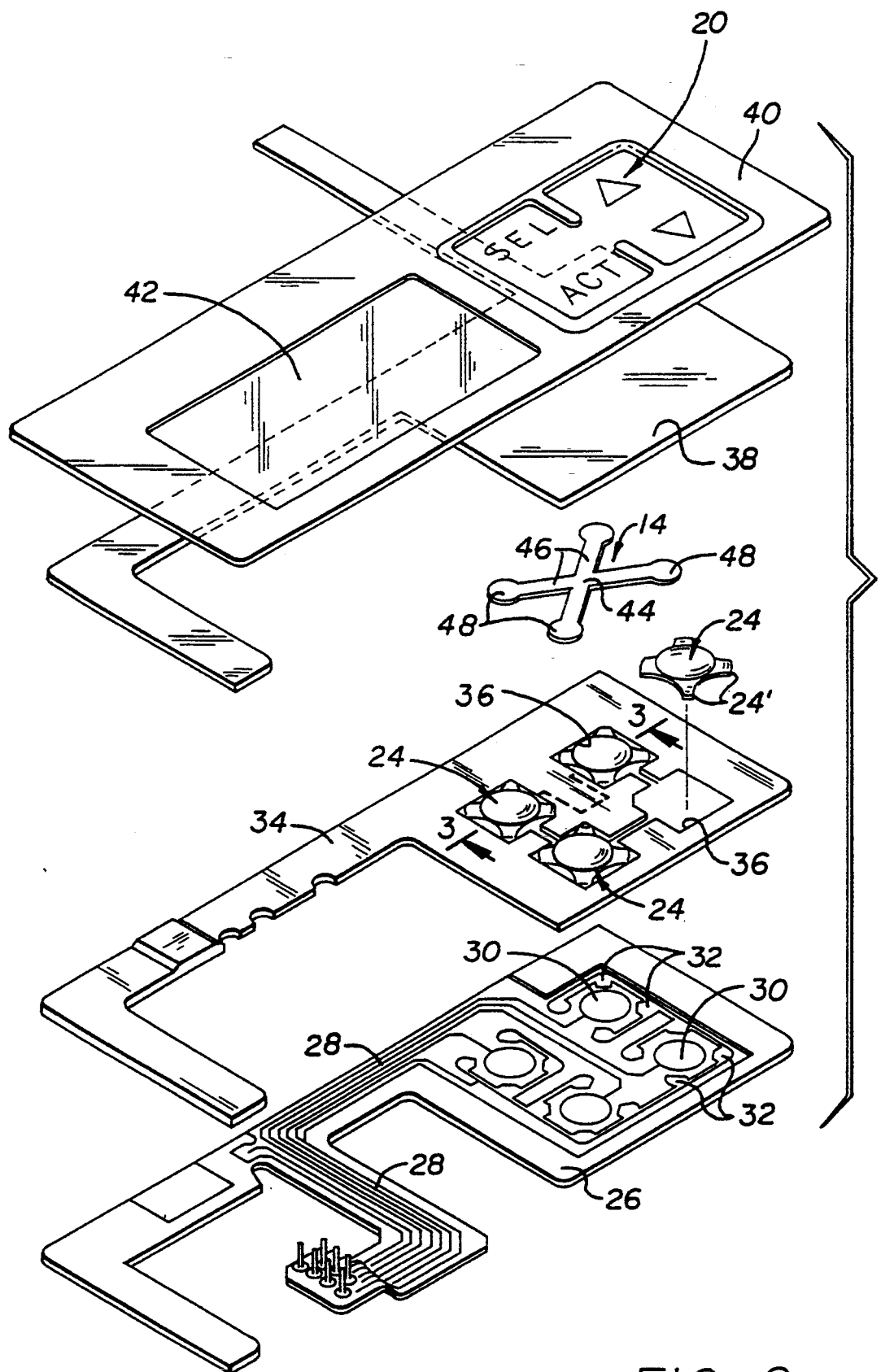
FIG. 2 is an exploded perspective view illustrating a plurality of improved membrane dome switches formed in accordance with the present invention, for use in the medication infusion pump depicted in FIG. 1.

As shown in the exemplary drawings, a plurality of improved membrane dome switches each of which is referred to generally by the reference numeral 10 (FIGS. 2 and 3) are provided for use in operating an electronic device, such as the illustrative medication infusion pump 12 shown in FIG. 1. The membrane dome switches 10 each include a tactile feel regulator shim 14 which provides each assembled membrane dome switch 10 with a positive and easily detected tactile feedback sensation in response to fingertip switch depression.

The membrane dome switch 10 of the present invention is shown in FIG. 1 in a typical medical instrumentation application, such as a medication infusion pump of the type marketed by MiniMed Technologies, Ltd. of Sylmar, Calif. under Model No. 506. The medication infusion pump 12 includes a compact pump housing 16 encasing appropriate programmable electrical and electronic components for delivering a medication such as insulin through a catheter 18 to a patient (not shown). A switch panel 20 on the pump housing 16 includes a plurality of membrane dome switches 10 formed in accordance with the invention, for use in programming and operating the electronic device.

In this regard, the switch panel 20 is normally manipulated in association with a visual display 22, which typically includes a liquid crystal or similar numeric and/or alpha-numeric indicia. Although the improved membrane dome switches 10 of the present invention are shown and described herein in conjunction with the medication infusion pump 12, it will be understood that the invention may be employed in a wide range of electronic devices utilizing one or more membrane dome switches.

As shown in more detail in FIGS. 2 and 3, a plurality of the improved membrane dome switches 10 are defined by conductive spring members 24 mounted in a sandwich or laminant manner within a plurality of membrane-like layers. The conductive spring members 24 are manually deformable by fingertip pressure applied to selected points or regions of the switch panel 20 to perform an electronic switching function.

More particularly, a circuit layer 26 is provided within the pump housing 16 of the medication infusion pump 12. In a typical construction, the circuit layer 26 comprises a relatively stiff sheet of insulative material such as polyimide, with one example of this material being the material marketed by DuPont under the trademark Kapton. The polyimide sheet has a conductive circuit pattern 28 formed on the upper surface thereof. The conductive circuit pattern 28 includes an array of switch pads 30 and 32 formed in groups to be associated with a respective one of the conductive spring members 24, as will be described.

The illustrative drawings show each group of switch pads 30 and 32 to include a relatively large centrally located switch pad 30, surrounded by a plurality of smaller cooperatively outlying switch pads 32. From the switch pads 30 and 32, the conductive circuit pattern 28 leads to a connector 33 for plug-in connection to other circuit components such as a circuit board (not shown) contained within the pump housing 16. The circuit layer 26 can be structurally reinforced by stiff backing layers (not shown), or it may otherwise be mounted within the pump housing 16 in a manner providing a relatively stiff and sturdy structure capable of withstanding normal fingertip pressure applied to the membrane dome switches 10.

The central portion of the conductive spring members 24 are shown in the form of curved or dome-shaped spring disks. The conductive spring members 24 are thus constructed from a conductive material to have a downwardly concave and upwardly convex geometry. The lower peripheral edge of each conductive spring member 24 is defined by an equiangular spaced group of four downwardly projecting legs 25. The diametric size of each conductive spring member 24, including the downwardly projecting legs 25, is chosen to correspond with an associated one of the groups of switch pads 30 and 32 on the circuit layer 26.

That is, as shown best in FIG. 3, each conductive spring member 24 is positioned on the circuit layer 26 with the downwardly projecting legs 25 in contact with the smaller outlying switch pads 32, and with the upwardly projecting central dome portion normally spaced above the larger centrally located switch pad 30. The conductive spring member 24 is downwardly deformable with an over-center snap action to contact the larger centrally located switch pad 30 and thereby close a circuit path between the switch pads 30 and 32 for purposes of operating the electronic device. Upon release of fingertip pressure applied to the conductive spring member 24, the central portion of the disk will return by spring action to a position spaced above the larger centrally located switch pad 30.

The four conductive spring members 24 shown in the drawings are physically retained in aligned relation with the switch pad groups on the circuit layer 26 by means of a retainer layer 34. This retainer layer 34 is formed from a suitable nonconductive material of selected sheet thickness, such as polyester or polycarbonate film, and is suitably attached to the circuit layer 26 by a pressure sensitive adhesive or the like.

A plurality of cut-outs or apertures 36 are formed in the retainer layer 34 in positions aligned respectively over the switch pads 30 and 32. Each of these apertures 36 is shown with a generally square shape to receive and retain an associated one of conductive spring members 24 in an orientation with the downwardly projecting legs 25 contacting the smaller outlying switch pads 32.

In accordance with conventional membrane dome switch design, the retainer layer 34 is covered in turn by an overlying shield layer 38. In a typical construction, the shield layer 38 may have a multi-layer geometry, including a nonconductive underside engaging the retainer layer 34 and the domed central regions of the conductive spring members 24, in combination with a conductive foil upper side. The shield layer 38 is attached by a suitable pressure sensitive adhesive or the like to the retainer layer.

The shield layer 38 is covered in turn by a display panel 40, which forms a portion of the pump housing 16 of the medication infusion pump 12. This display panel 40 includes the switch panel 20 in the form of a graphics overlay membrane having suitable indicia positioned in alignment over the plurality of conductive spring members 24. In addition, as shown, the display panel 40 includes a transparent window 42 to permit viewing of the visual display 22 (FIG. 1).

The tactile feel regulator shim 14 comprises an additional element incorporating into the dome switch assembly, to provide a user with an easily detectable tactile feedback sensation when each dome switch is depressed. FIG. 2 illustrates the tactile feel regulator shim 14 in one preferred geometry as a generally X-shaped web of nonconductive sheet or film material, such as polyester or polycarbonate plastic. This web has a multi-legged configuration defining a central anchor portion 44 secured as by an adhesive to the retainer layer 34 at a position disposed centrally within the group of the conductive spring members 24.

A plurality of narrow and relatively flexible outwardly projecting legs 46 extend outwardly from the central anchor portion 44 and terminate in foot pads 48 respectively positioned generally over the conductive spring members 24. Importantly, these foot pads 48 define small shims which are unattached to the underlying conductive spring members 24 or to the overlying shield layer 38. The tactile feel regulator shim 14 is disposed between the retainer layer 34 and the shield layer 38 in a pocket or cavity wherein the shield layer is not secured to the retainer layer.

In use, the display panel 40 and the shield layer 38 are sufficiently deformable in a direction perpendicular to their planes to deform the conductive spring members 24 for purposes of operating and/or programming the medication infusion pump 12. That is, fingertip pressure applied to a selected region of the display panel 40 is effective to deform the underlying conductive spring member 24 with an over-center snap action to achieve momentary closure of the circuit path on the circuit layer 26 associated with that spring disk.

The design of the tactile feel regulator shim 14 thereby both significantly enhances tactile feedback, and requires less mechanical travel of the display panel 40 and the shield layer 38 to cause the switching action. It should also be noted that the tactile feel regulator shim 14 does not change the mechanical quality or characteristics of the display panel 40 or the shield layer 38.

Importantly, the foot pads 48 interposed between the shield layer 38 and the selected conductive spring members 24 has been found to yield a significantly enhanced, easily detected and highly consistent, tactile fingertip feedback sensation to provide the user with positive confirmation of proper switch actuation. This easily detected tactile feedback remains consistent throughout a range of typical manufacturing tolerance variations in the height of each conductive spring member 24. However, if necessary or desirable, the thickness of the retainer layer 34 and/or the thickness of the tactile feel regulator shim 14 can be altered as appropriate to provide a custom tailored tactile feedback sensation.

Figure 4:
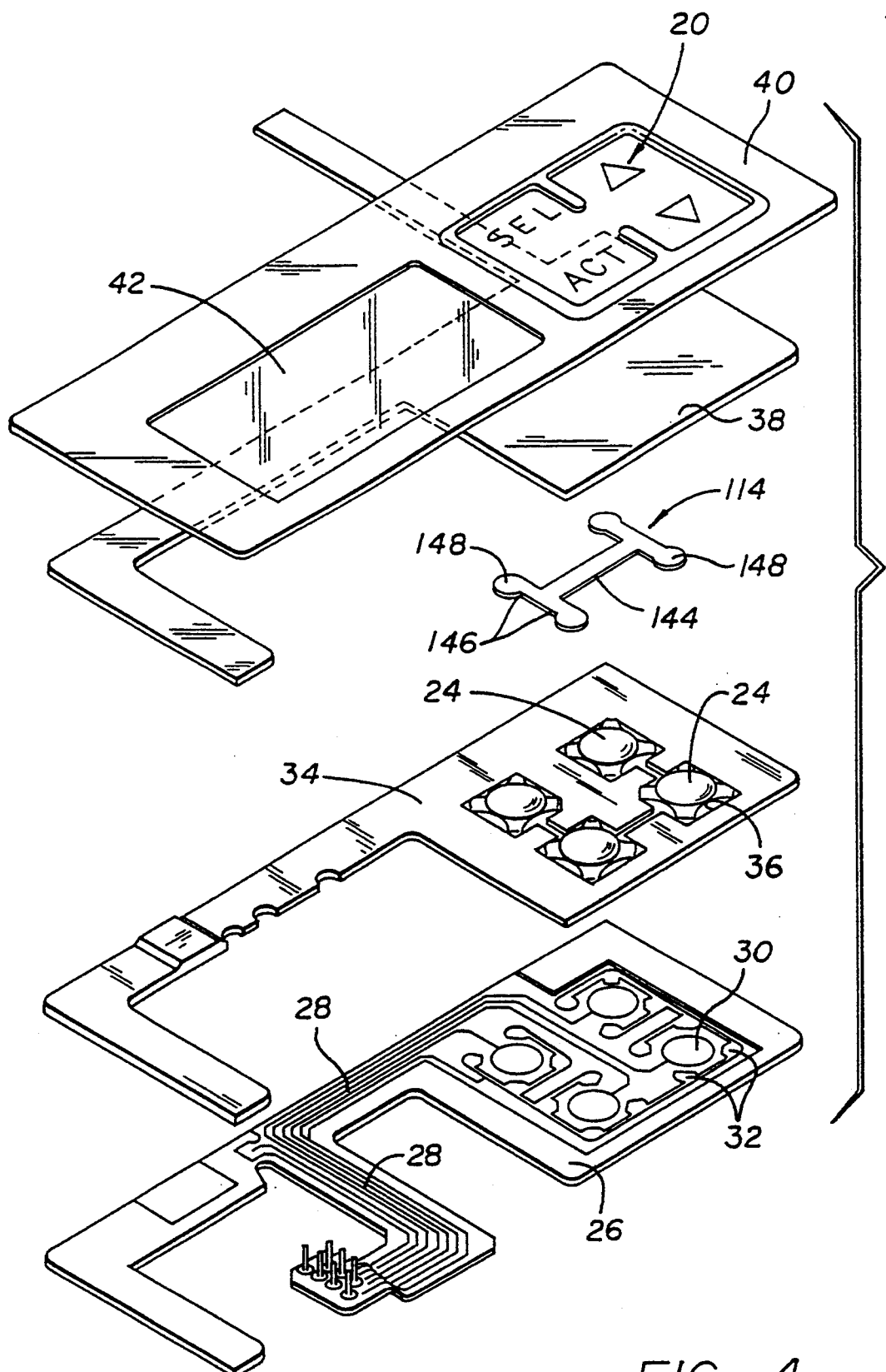
FIG. 4 is an exploded perspective view illustrating an alternative preferred form of the invention.

FIG. 4 shows an alternative preferred form of the invention wherein components corresponding with those shown and described in FIGS. 1-3 are identified by common reference numerals. As shown, a modified tactile feedback regulator shim 114 is provided with a generally H-shaped configuration. In this embodiment, a central anchor portion 144 of the tactile feedback regulator shim 114 is suitably attached to the retainer layer 34, with outwardly projecting legs 146 terminating in foot pads 148 positioned over the conductive spring members 24.

It may therefore be appreciated from the above detailed description of the preferred embodiment of the present invention that it teaches an improved membrane dome switch having a positive and easily detected tactile feedback sensation which is provided to the user notwithstanding normal dimensional variations present in domed spring disks. The advantages and objectives of the membrane domed switch of the present invention are achieved without incurring any substantial relative disadvantage.

Although an exemplary embodiment of the present invention has been shown and described with reference to particular embodiments and applications thereof, it will be apparent to those having ordinary skill in the art that a number of changes, modifications, or alterations to the invention as described herein may be made, none of which depart from the spirit or scope of the present invention. All such changes, modifications, and alterations should therefore be seen as being within the scope of the present invention.

What is claimed is:

1. A membrane dome switch assembly comprising:
   a circuit layer having a conductive pattern thereon;
   a plurality of domed spring disks;
   a retainer layer secured to said circuit layer and having a plurality of apertures formed therein, said spring disks being received respectively within said apertures;
   at least one cover layer secured to said retainer layer and cooperating therewith to retain said spring disks in aligned relation with said circuit layer; and
   a tactile feel regulator shim including an anchor portion interposed between said cover layer and said retainer layer and a plurality of outwardly projecting legs respectively terminating in foot pads interposed between said spring disks and said cover layer, said spring disks being selectively deformable in response to fingertip pressure applied to said cover layer to depress said spring disks, with an easily detected tactile feedback sensation, against said circuit layer to close a circuit portion defined by said circuit pattern.

2. A membrane dome switch assembly as defined in claim 1, wherein said cover layer has graphics indicia located thereon.

3. A membrane dome switch assembly as defined in claim 1, wherein said cover layer comprises:
   a shield layer overlying said spring member; and
   a graphics membrane overlying said shield layer and having graphics indicia located thereon.

4. A membrane dome switch assembly as defined in claim 1, wherein said anchor portion of said shim is secured to said retainer layer, and wherein said foot pads are unconnected to said spring disks.

* * * * *